United States Patent [19]

Gilby

[11] 4,035,963
[45] July 19, 1977

[54] METHOD OF FORMING DUAL MIRRORS

[75] Inventor: Anthony C. Gilby, Darien, Conn.

[73] Assignee: Wilks Scientific Corporation, South Norwalk, Conn.

[21] Appl. No.: 702,214

[22] Filed: July 2, 1976

[51] Int. Cl.$^2$ .............................................. B24B 1/00
[52] U.S. Cl. ...................................... 51/324; 72/324; 72/341; 350/320
[58] Field of Search ............... 72/324, 340, 341; 51/324, 281 R; 356/51, 244; 350/320, 189, 192

[56] References Cited

U.S. PATENT DOCUMENTS

| 3,726,598 | 4/1973 | Gilby et al. | 356/244 |
| 3,837,124 | 9/1974 | Johnson et al. | 51/324 X |
| 3,889,431 | 6/1975 | Johnson | 51/284 |
| 3,932,148 | 1/1976 | Krewalk | 51/284 R |

*Primary Examiner*—James R. Duzan
*Attorney, Agent, or Firm*—Buckles and Bramblett

[57] ABSTRACT

A method of forming a pair of identical spherical mirrors having their centers of curvature separated in space. A blank having substantially parallel planar front and rear surfaces is provided. The front surface is scored to divide it into two surface segments. The entire front surface is then ground to a spherical shape. The blank is then bent along the scored region to separate in space the centers of curvatures of each of the surface segments.

The foregoing abstract is not to be taken either as a complete exposition or as a limitation of the present invention. In order to understand the full nature and extent of the technical disclosure of this application, reference must be had to the following detailed description and the accompanying drawings as well as to the claims.

5 Claims, 4 Drawing Figures

METHOD OF FORMING DUAL MIRRORS

BACKGROUND OF THE INVENTION

In U.S. Pat. No. 3,726,598 which issued Apr. 10, 1973 to Anthony C. Gilby and James Alan Horton, there is disclosed a multiple pass optical absorption cell. The cell includes a pair of identical spherical objective mirrors at one end and a field mirror at the other. The two objective mirrors are positioned on a common mount such that their centers of curvature are separated by a fixed predetermined distance. The optical path length through the cell is changed by rotating the common mount but the distance between the centers of curvature remains fixed.

The multiple pass cell disclosed in the above-mentioned patent represented an important advance over cells known to the prior art and has been an outstanding commercial success. However, it would be desirable to simplify the construction, particularly, the construction of the objective mirror arrangement. In the patent, the two identical spherical objective mirrors are independently mounted upon an angled mirror mount which maintains the centers of curvature of the mirrors separated by the desired distance. It would be desirable to eliminate this mounting step. The mounting step also introduces the possibility of vertical misalignment and, accordingly, additional rigidity between the two objective mirrors is desirable.

Accordingly, it is a primary object of the present invention to provide a plurality of individual spherical mirrors having their centers of curvature separated in space while avoiding the need for making individual mirror adjustments.

Another object is to simplify the grinding and polishing of such a mirror pair.

Another object is to provide such a pair of mirrors wherein the tendency of the mirrors to tilt vertically is tightly constrained.

Other objects, features and advantages will be apparent from the following description and appended claims.

SUMMARY OF THE INVENTION

The objects of this invention are achieved by a novel method of forming a plurality of identical spherical mirrors having their centers of curvature separated in space. A blank is provided which has front and back surfaces. The front surface of the blank is scored to divide the surface into at least two surface segments. The front surface is formed to a spherical shape, each of the surface segments defining a different portion of the surface of a common sphere. The blank is bent where scored to separate in space the centers of curvature of each of the surface segments.

DESCRIPTION OF THE PREFERRED EMBODIMENT

Figure 1:
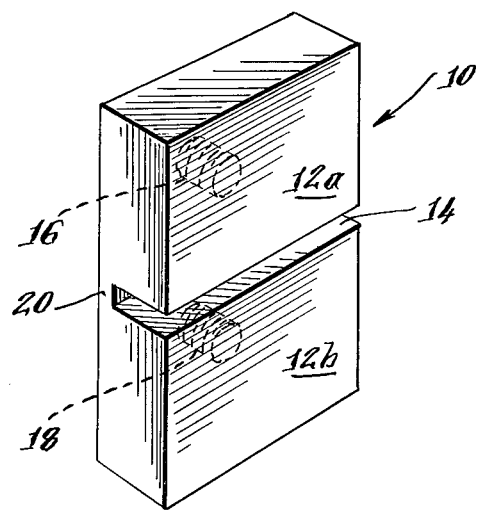
FIG. 1 is a perspective view of a blank usable in the method of this invention.

With particular reference to FIG. 1, there is illustrated an objective mirror blank 10 which includes a planar front surface divided into two front surface segments 12a, 12b by means of a central cut or score 14. The blank 10 may be of any suitable material such as aluminum and its back surface includes a pair of mounting holes 16, 18 which extend into those portions, respectively, of the blank behind the segments 12a, 12b. The depth of the score 14 is not critical, but in one embodiment the thickness of the blank 10 is 0.220 inch and the score 14 has a depth of 0.180 inch leaving a 0.040 inch web 20 joining the two segments.

Figure 2:
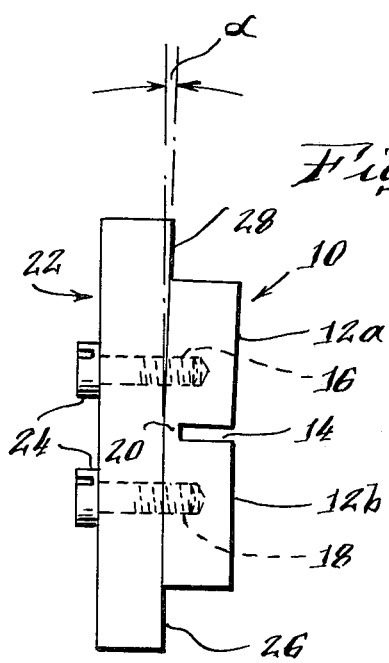
FIG. 2 is a side view of the blank of FIG. 1 shown mounted on a grinding fixture.
Figure 3:
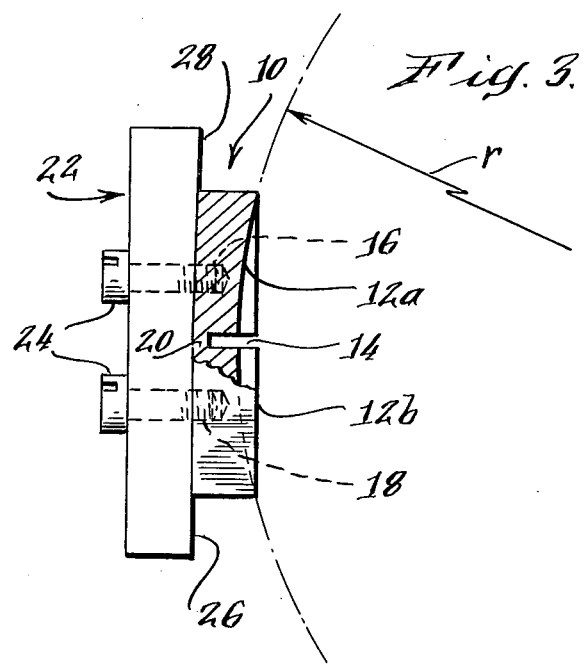
FIG. 3 is a view similar to FIG. 2 but with the blank partially broken away and showing the blank after the grinding step of the method of the invention; and, FIG. 4 is a plan view of a long path cell with the mirror of FIG. 3 mounted therein.

The next step of the method is illustrated in FIG. 2 wherein the blank 10 is shown mounted on a grinding fixture 22 by means of a pair of mounting bolts 24. The mounting surface of fixture 22 is slightly V-shaped to provide a lower mounting surface 26 and an upper mounting surface 28 forming a slight angle $\alpha$ thereto, the apex of the V being positioned beneath the web 20. With the bolts 24 tightly drawn, the blank 10 is caused to be bent slightly at the web 20. The angle $\alpha$ may, of course, be varied to suit the conditions. However, in the specific embodiment previously referred to, it has a value of 1.1°. After mounting upon the fixture 22, the front surface of the blank 10 is ground by conventional means, as illustrated in FIG. 3, to a single, spherical surface of radius $r$ which, in the specific embodiment described, is 50 millimeters. After grinding, the aluminum blank may be suitably finished, such as by nickel plating, optical polishing, and gold coating, to provide a reflective surface.

Figure 4:
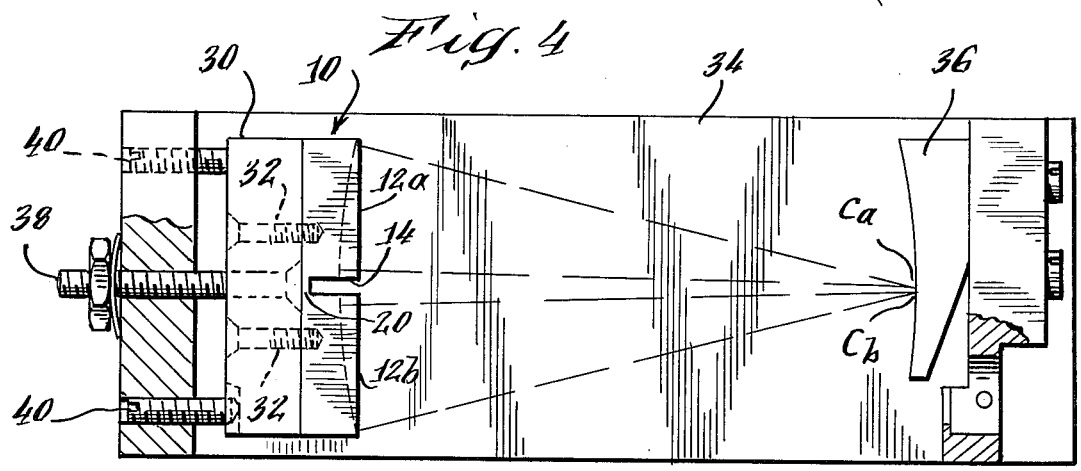

After the reflective surface has been formed as shown in FIG. 3, the blank 10 is removed from the grinding fixture 22 and is securely mounted to a flat mounting plate 30 (FIG. 4) by means of the mounting screws 32 extending into the tapped holes 16–18. Tightening of the screws 32 flattens the mirror 10 so that the individual mirror segments 12a, 12b are rotated slightly apart causing their centers of curvature $C_a$, $C_b$ to be separated slightly in space as shown. FIG. 4 further illustrates the mirror 10 as mounted in a long path cell comprising a base plate 34, a field mirror 36 and suitable mounting 38 and adjusting 40 screws, as required. Further details of the construction and operation of such a long path cell will be found in the above mentioned patent of Gilby and Horton.

It is believed that the advantages of the disclosed method will now be apparent to those skilled in the art. The actual construction of the objective mirrors is greatly simplified and resistance to tilting between the mirror segments is greatly increased due to the stiffness of the web 20. It will also be apparent that a number of variations and modifications may be made in this invention without departing from its spirit and scope. In one such modification, for example, the grinding fixture could be flat but the mounting plate could have a V-shaped surface. Accordingly, the foregoing description is to be construed as illustrative only, rather than limiting. This invention is limited only by the scope of the following claims.

I claim:

1. The method of forming a plurality of identical spherical mirrors having their centers of curvature separated in space which comprises: providing a blank having front and back surfaces; linearly scoring the front surface of said blank to divide said front surface into at least two surface segments; forming said front surface to a spherical shape, each of said surface segments defining a different portion of the surface of a common sphere; and bending said blank substantially solely where scored to separate in space the centers of curvature of each of said surface segments without substantially altering the spherical surface defined by either of said surface segments.

2. The method of claim 1 wherein said forming step comprises: mounting said blank with its back surface secured to a fixture; and grinding said front surface while said blank is so mounted.

3. The method of claim 2 wherein said bending step comprises: mounting said blank with its back surface secured to a mounting plate, one of said fixture and mounting plates being non-planar.

4. The method of claim 1 wherein said bending step comprises: mounting said blank with its back surface secured to a mounting plate.

5. The method of forming a pair of identical spherical mirrors having their centers of curvature separated in space which comprises: providing a blank having substantially parallel front and back major surfaces; forming said front major surface to a spherical shape; and bending said blank along a substantially straight line to form two blank segments, each of said segments including a substantially unaltered portion of said spherical front surface, whereby the centers of curvature of said front surface portions are separated in space.

* * * * *